(12) United States Patent
Eller et al.

(10) Patent No.: US 10,170,204 B1
(45) Date of Patent: Jan. 1, 2019

(54) METHODS, SYSTEMS, AND TOOLS FOR USE IN PROCESSING PRESCRIPTIONS

(75) Inventors: Charles E. Eller, Lake St. Louis, MO (US); Andrew Cox, University City, MO (US); Brian David Fruchter, Eureka, MO (US)

(73) Assignee: EXPRESS SCRIPTS STRATEGIC DEVELOPMENT, INC., St. Louis, MO (US)

( * ) Notice: Subject to any disclaimer, the term of this patent is extended or adjusted under 35 U.S.C. 154(b) by 54 days.

(21) Appl. No.: 12/828,114

(22) Filed: Jun. 30, 2010

Related U.S. Application Data

(60) Provisional application No. 61/269,841, filed on Jun. 30, 2009.

(51) Int. Cl.
*G16H 20/00* (2018.01)
*G16H 20/10* (2018.01)

(52) U.S. Cl.
CPC ................... *G16H 20/10* (2018.01)

(58) Field of Classification Search
CPC ..... G06C 50/22; G06C 50/24; G06F 19/3456; G06F 11/324; G06F 19/3462; G06F 19/3475; G06Q 50/22; G06Q 50/24; G06Q 10/087; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | | |
|---|---|---|---|---|
| 5,937,422 | A * | 8/1999 | Nelson et al. | 715/206 |
| 5,950,630 | A * | 9/1999 | Portwood et al. | 128/897 |
| 7,069,226 | B1 * | 6/2006 | Kleinfelter | 705/2 |
| 7,286,996 | B1 | 10/2007 | Fiedotin et al. | |
| 2003/0050802 | A1 * | 3/2003 | Jay et al. | 705/3 |

(Continued)

*Primary Examiner* — Joseph D Burgess
(74) *Attorney, Agent, or Firm* — Bryan Cave Leighton Paisner LLP

(57) ABSTRACT

The inventions disclosed herein include methods, systems, and tools for use in processing prescriptions. Among the benefits of these methods, systems, and tools are promotion of efficiency in filling prescriptions and reduction of errors. A heightened analysis element may be established that alerts a pharmaceutical professional to a particular component of a prescription (a prescription element) for special attention. An insignificant differences notice may de-emphasize certain prescription elements to inform a pharmaceutical professional that the information of such prescription elements is less critical. Methods of the present invention may be used to designate a prescription as a renewal, partial renewal, or partially equivalent renewal. The disclosed inventions include methods of creating and/or using such heightened analysis elements, insignificant differences notices, and/or designation of a prescription as a renewal, partial renewal, or partially equivalent renewal.

26 Claims, 10 Drawing Sheets

(56) References Cited

U.S. PATENT DOCUMENTS

| | | |
|---|---|---|
| 2003/0167189 A1* | 9/2003 | Lutgen et al. .................... 705/3 |
| 2003/0225595 A1* | 12/2003 | Helmus ................ G06Q 10/063 |
| | | 705/2 |
| 2004/0138921 A1* | 7/2004 | Broussard ............. G06F 19/326 |
| | | 705/2 |
| 2006/0100974 A1* | 5/2006 | Dieberger ............. G06F 11/324 |
| 2006/0229915 A1 | 10/2006 | Kosinski et al. |
| 2007/0088567 A1* | 4/2007 | Berkelhamer ...... G06F 19/3456 |
| | | 705/2 |
| 2008/0046294 A1 | 2/2008 | Fiedotin et al. |
| 2009/0009300 A1* | 1/2009 | Jarvis ................... G06Q 10/109 |
| | | 340/309.16 |
| 2009/0157424 A1* | 6/2009 | Hans ................................ 705/2 |
| 2009/0198518 A1* | 8/2009 | McKenzie et al. ............... 705/3 |
| 2010/0125461 A1* | 5/2010 | Heald et al. ...................... 705/2 |

* cited by examiner

FIG. 3

| User Name | | Input Screen | | | Invalid Rx |
|---|---|---|---|---|---|
| Member Information | | Missing | | | |
| ID Number | | ☐ | Coverage ID | [Coverage ID] | ☐ Fax – Verify Origin |
| Last Name | | ☐ | Administrator | [Administrator] | ☐ Fax – CII |
| First Name | | ☐ | Company | [Company] | ☐ NY control |
| Date of Birth | | ☐ | Group | [Group] | ☐ Not in System |
| Address | | ☐ | | View History | ☐ No Active Coverage |
| Drug Information | | Clarify | | | Invalid Rx |
| Date Written | [Date Written] | | | | ☐ Refill too soon |
| Item | [Item] | ☐ | | | ☐ Expired refill |
| Strength | [Strength – auto populated] | ☐ | | | ☐ Hold for Future fill |
| Form | [Form – auto populated] | ☐ | | | ☐ OTC |
| Signal Code | [Signal Code] | ☐ | | | ☐ Duplicate Order |
| SIG Translation | [Signal Code translation – auto populated] | ☐ ☐ ☐ | | | ☐ MBO – Mfg backorder |
| Dispense Information | | | | | ☐ CII - Diagnosis Code |
| Qty Prescribed | [Qty Prescribed] | | | | ☐ DMB – Discontinued Backorder ← 30 |
| Qty Dispensed | [Qty Dispensed] | | | | |
| Days Supply | [Days Supply] | | | | |
| Max Days Supply | [Max Days Supply] | | | | |
| # of Refills | [# of Refills] | | | | |
| DAW | [DAW] | | | | |
| Prescriber Information | | | | | Invalid Rx |
| DEA Number | [DEA #] | | | | ☐ Stamped Signature |
| Last Name | [Last Name] | | | | ☐ Missing Signature |
| First Name | [First Name] | | | | ☐ Illegible Signature |
| Address | [Address] | | | | ☐ Expired DEA # |
| Phone Number | [Phone #] | | | | ☐ Missing DEA for CII |
| Fax Number | [Fax #] | | | | |
| | | Complete Rx | | | |

| # | CONDITION |
|---|---|
| 1 | Renewal: Prescription must be a renewal, i.e. there has to be at least one prior prescription:<br>• For the Same Patient (Same Admin, Member ID, Patient Number)<br>• For a Similar Drug (Same GPI-10) |
| 2 | Equivalent SIG: The SIG of the prescription must have the same meaning as the SIG of its corresponding prior prescription. |
| 3 | Same Doctor: The prescription and its corresponding prior prescription must be subscribed by the same doctor.<br>• This condition is currently verified as follows: (Same doctor DEA) or (same doctor last name and same doctor ZIP) |
| 4 | Same Drug Form: The drugs prescribed in this prescription and in its corresponding prior prescription must have the same form. |
| 5 | Not DAW: The prescription should not indicate "Dispense as Written (DAW)" for the prescribed drug. |
| 6 | Same Strength: The drugs prescribed in this prescription and in its corresponding prior prescription must have the same strength. |
| 7 | Same Prescribed Quantity: The drugs prescribed in this prescription and in its corresponding prior prescription must be prescribed for the same amount/quantity. |
| 8 | Not a Controlled Substance: The prescribed drug must not be a controlled substance. |

Fig. 6

| ITEM NAME | STRENGTH | FORM CODE | FORM TYPE | NDC | GCN SEQ. NO | GCN-GROUP # |
|---|---|---|---|---|---|---|
| AMLODIPINE BESY/BENAZEPRIL | 5MG-20MG | CAP | E | 000937372WA | 023768 | 1 |
| AMLODIPINE/BENAZEPRIL | 5MG-20MG | CAP | E | 00781227301 | 023768 | 1 |
| LOTREL | 5/20 | CAP | E | 00078040605 | 023768 | 1 |
| AMLODIPINE BESY/BENAZEPRIL | 5MG-10MG | CAP | E | 000937371WA | 023769 | 1 |
| AMLODIPINE BESY/BENAZEPRIL | 5MG-10MG | CAP | E | 0009373101 | 023769 | 1 |
| AMLODIPINE/BENAZEPRIL | 5MG-10MG | CAP | E | 00781227201 | 023769 | 1 |
| LOTREL | 5/20 | CAP | E | 00078040505 | 023769 | 1 |
| AMLODIPINE BESY/BENAZEPRIL | 2.5MG-10MG | CAP | E | 00093737001 | 023770 | 1 |
| AMLODIPINE/BENAZEPRIL | 2.5MG-10MG | CAP | E | 00781227101 | 023770 | 1 |
| LOTREL | 2.5/10 | CAP | E | 00078040405 | 023770 | 1 |
| LOPRESSOR HCT | 100/25 | TAB | E | 00078046105 | 00412 | 2 |
| LOPRESSOR HCT | 50/25 | TAB | E | 00078046005 | 00413 | 2 |
| METOPROLOL/HCTZ | 50/25MG | TAB | E | 00378042401 | 00413 | 2 |
| METOPROLOL/HCTZ | 100/55 | TAB | E | 00378044501 | 00414 | 2 |

FIG. 7

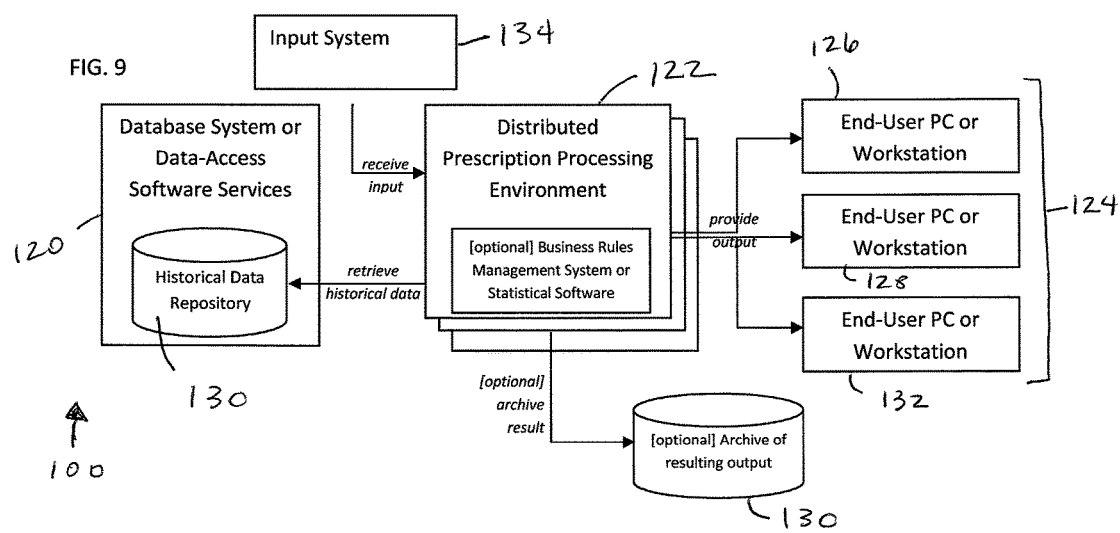

METHODS, SYSTEMS, AND TOOLS FOR USE IN PROCESSING PRESCRIPTIONS

RELATED APPLICATION INFORMATION

This application claims the benefit of U.S. Provisional Patent Application Ser. No. 61/269,841, filed on Jun. 30, 2009, the disclosure of which is incorporated herein by reference in its entirety for all purposes.

BACKGROUND OF THE INVENTION

As is well known, prescriptions are used by a physician, dentist, podiatrist, optometrist, and/or other medical professional with prescribing powers under applicable state law (a "prescribing professional") to prescribe one or more drugs and/or other medical devices ("drugs") for a patient. Via a prescription, a prescribing professional conveys, transmits, or otherwise provides information regarding certain prescription elements to one or more persons and/or entities who will fulfill the prescription and dispense the prescribed drug. Prescription elements may include: (1) patient elements, (2) drug elements, (3) dispensing elements, and/or (4) prescriber elements.

Patient elements may include patient identification elements, such as name, address, the age, date of birth, and/or gender. A unique identifier, e.g., a unique number created for a patient by a pharmacy, may be a patient identification element. Patient elements may also include patient health care coverage elements, such as insurer, policy number, group insurance and/or member number, employer, and/or health plan administrator. Finally, patient elements may include patient health elements such as chronic health conditions, prescription drug history, and/or other medical history.

Drug elements might include items such as the name of the drug; the strength; the form; instructions to the patient regarding how, how much, when, and for how long the drug should be administered (e.g., the "Sig"); and/or other information regarding the prescribed drug, such as compounding instructions. Other drug elements might include information not typically provided directly with a prescription, but obtainable based on information that is provided with the prescription, such as a national drug code ("NDC") number; a generic code number ("GCN"), referring to a number assigned to each drug by First Data Bank, Inc.; and/or a generic product identifier ("GPI"), referring to the number provided by Medi-Span (a part of Wolters Kluwer Health).

Dispensing elements may include, inter alia, the quantity prescribed, the quantity dispensed, the number of days' supply, the number of refills, whether generic substitutions are permitted, e.g., whether or not the prescription must be "dispensed as written" or "DAW."

Prescriber elements refers to information about the prescribing professional, such as name, address, Drug Enforcement Agency ("DEA") number, facsimile number, medical group (or other professional association), and the like.

A prescription will include and/or otherwise provide "prescription element information," i.e., information specific to a plurality of prescription elements. Prescription element information may be provided by one or more data points specifically included in the prescription, e.g., a patient's name. In other instances, prescription element information may be obtained, identified, or otherwise established based on one or more data points specifically included in the prescription, e.g., a patient's name and address may be used by a pharmaceutical professional to obtain, identify, or otherwise establish a patient's identification number. By way of further example, drug name, form, and strength may be used to establish the NDC of the prescribed drug.

Thus, references to "prescription element information" should be broadly understood and refers to and includes information (e.g., one or more data points) obtained, identified, or otherwise established, directly or indirectly, from a prescription that is relevant to one or more specific prescription elements. Furthermore, references to prescription element information for a particular prescription element refers to such prescription element information regardless of the format such information may take, e.g., human-readable, computer-readable, or otherwise. A particular prescription may omit information for some prescription elements.

It is generally understood that "processing a prescription" typically begins with a prescribing professional deciding upon or otherwise selecting a drug for a patient and typically ends with receipt by the patient, the patient's caregiver and/or other representative of the patient (collectively and/or individually, unless the context otherwise requires, the "patient") of the drug.

"Prescription" as used herein should be broadly understood to refer to and include any method by which a prescribing professional does and/or may prescribe one or more drugs for a patient, regardless of the form or manner of the prescription and regardless of whether the prescription is in tangible form, intangible, or both. Furthermore, reference to "a prescription", "the prescription", and the like should be broadly understood to refer to and include any and all manifestations and/or embodiments of that prescription. Thus, if a prescribing professional faxes a written prescription to a pharmacy, which the pharmacy then uses to create an electronic version of the prescription, "the prescription," "a prescription," and the like shall refer to any and all copies, versions, and/or embodiments of such prescription and/or the prescription element information of such prescription, unless the context specifically requires otherwise.

Typically, processing a prescription will include one or more steps via which a pharmacist, often with assistance of other professionals (pharmacists and/or such other professionals are referred to herein individually as a "pharmaceutical professional") and often working at or for a pharmacy, will evaluate, fill, and/or dispense a prescribed drug to a patient. Of course, a pharmaceutical professional may provide other services, such as counseling the patient and/or assisting with therapy compliance. Processing a prescription may also include one or more steps, (1) in which a patient's health insurance is evaluated to determine, e.g., whether the prescribed drug is covered by the patient's health insurance; (2) in which a claim is made with one or more health insurance companies, drug manufacturers, and/or distributors for payment or partial payment; and/or (3) in which payment from the patient is received or otherwise processed.

The details of how a prescription gets from a prescribing professional to a to pharmaceutical professional vary widely. In some instances, the patient may act as an intermediary; for example, a prescribing professional may give a written prescription to a patient who then delivers it to a pharmacy and/or pharmaceutical professional in person or who otherwise transmits, conveys, or delivers the prescription to a pharmacy and/or pharmaceutical professional. In other instances, a prescription may be transmitted, conveyed, or otherwise delivered to a pharmacy and/or pharmaceutical professional more or less directly by a prescribing professional For example, a prescribing professional may submit an electronic prescription, e.g., via the Internet or other wired or wireless system in communication with a system accessible at or by a pharmacy and/or pharmaceutical professional; a prescribing professional may submit a prescription via telephone; and/or a prescribing professional may fax, mail, and/or otherwise transmit, convey, or deliver a prescription to a pharmacy and/or pharmaceutical professional. Again, "the prescription" delivered to the pharmacy and/or pharmaceutical professional may refer, for example, to a written prescription given or otherwise delivered to the patient by the prescribing professional or it may refer to a duplicate of that prescription, such as a facsimile or other electronic copy and/or to an alternative embodiment of some or all of the information provided by that prescription, i.e., to some or all of the prescription element information associated with one or more prescription elements.

In some instances, a prescribing professional may dispense and/or administer a drug directly to a patient.

Similarly, the details of how a prescribed drug gets from a pharmacy or prescribing professional to a patient may vary. The patient may pick up the prescribed drug at a pharmacy (which may or may not be the pharmacy by which the prescription was originally received), physician's office, hospital, or other location. Alternatively, the pharmacy may deliver the prescribed drug to the patient via mail, messenger service, or otherwise.

Verification of a prescription by a pharmaceutical professional and/or verification by a pharmaceutical professional that a dispensed drug is the prescribed drug are common steps in processing a prescription, and such verification steps help minimize errors in processing prescriptions. However, not all errors are readily detectable via such verification steps and, in any event, errors can and do occur at any one or more of the steps that may be involved in processing a particular prescription, sometimes with serious consequences.

Errors in processing a prescription can occur when a prescribing professional creates the prescription; for example, the prescribing professional may include prescription element information that is incorrect. Other errors may occur after a prescription has been received by a pharmacy and/or pharmaceutical professional has received a prescription; for example, correct prescription information from the prescription may be incorrectly entered upon creation of an electronic version of the prescription to become incorrect prescription element information. "Errors" may also refer to instances in which the prescription element information provided by the prescribing professional is "correct", e.g., it accurately reflects the intent of the prescribing professional and is correctly entered and/or processed by pharmaceutical professionals, but administering the prescribed drug, at the designated strength, form, and/or in accordance with the instructions would be inappropriate, unsafe, and/or otherwise undesirable, either generally or for the particular patient—such errors may be referred to as "misprescribed drug errors"

Thus, a need exists for methods of processing prescriptions that (1) minimize errors in processing and/or filling prescriptions and/or in dispensing drugs by a pharmacy and/or pharmaceutical professional, (2) improve identification of incorrect prescription element information, and/or (3) improve identification of misprescribed drug errors.

In addition, a need exists for methods of processing prescriptions that are more efficient than prior art methods and that maximize the benefits of the skills and training of pharmaceutical professionals.

BRIEF SUMMARY OF THE INVENTION

An invention having various embodiments that meet one or more of those needs has now been developed. Embodiments of this invention include methods for processing prescriptions and/or prescription claims (generally referred to herein as "prescriptions").

In one aspect, the present invention concerns a method of processing a prescription, the method comprising: (a) obtaining a new prescription; (b) obtaining a set of historical prescriptions; (c) obtaining from the set of historical prescriptions at least one similar historical prescription; (d) obtaining, based on a comparison of the new prescription to the similar historical prescription, a heightened analysis element or an insignificant differences notice.

In yet another aspect, the present invention concerns a method of selecting a prescription for processing as a renewal, the method comprising: (a) obtaining a new prescription; (b) obtaining a set of historical prescriptions; (c) obtaining from the set of historical prescriptions at least one similar historical prescription; (d) if the similar historical prescription is for the same patient and a similar drug, processing the new prescription as a renewal of the similar historical prescription.

In a further aspect, the present invention concerns a computer-implemented method of using a database of historical prescriptions to process a new prescription, the new prescription comprising new prescription element information, the method comprising: (a) receiving the new prescription element information; (b) analyzing the database of historical prescriptions to identify at least one similar historical prescription; (c) comparing the new prescription element information to the at least one similar historical prescription; (d) generating at least one of a heightened analysis element and an insignificant differences notice; and (e) presenting the at least one of a heightened analysis element and an insignificant differences notice to a user for analysis by displaying visual indicators, wherein the visual indicators comprise a visual representation of the at least one of a heightened analysis element and an insignificant differences notice.

In another aspect of the invention, a pharmaceutical professional uses an insignificant differences notice and/or a heightened analysis element as a tool to reduce and/or identify errors and/or to increase efficiencies in processing a prescription.

Another aspect of the invention comprises (a) a database system configured to receive and store data for prescription element information of a set of historical prescriptions; and (b) a distributed processing environment in communication with the database system and configured to: (i) receive input of prescription element information of a new prescription; (ii) perform one or more procedures to compare the prescription element information of the new prescription to the prescription element information of the set of historical prescription; (iii) perform one or more procedures to establish at least one historical prescription as a similar historical prescription; and (iv) perform one or more procedures to establish at least one of a heightened analysis element or an insignificant difference notice based on a comparison of the prescription element information of the new prescription to the prescription element information of the at least one similar historical prescription.

Optionally, such a system of the invention may also include a workstation system in communication with the distributed processing environment and configured to receive a heightened analysis element and/or insignificant differences notice from the distributed processing environment; provide an indicator of the heightened analysis element and/or insignificant differences notice to a user; receive as input the prescription element information of the new prescription; and/or to provide the prescription element information of the new prescription to the distributed processing environment.

Another optional feature of such a system of the invention is an input system in communication with the distributed processing environment and configured to receive as input the prescription element information of the new prescription and to provide the prescription element information of the new prescription to the distributed processing environment.

In another aspect, a tool of the invention for use in processing a new prescription comprises (a) a similar historical prescription, wherein the similar historical prescription comprises historical prescription element information; (b) one or more procedures for establishing relationships between the new prescription element information and the historical prescription element information; and (c) one or more procedures for establishing at least one of an insignificant differences notice or a heightened analysis element based on the based on the relationships between the new prescription element information and the historical prescription element information.

BRIEF DESCRIPTION OF THE DRAWINGS

To facilitate further description of the invention, the following drawings are provided in which:

FIG. 3 is an illustration of an exemplary input screen for use in an embodiment of a method of this invention;

FIG. 5 is an illustration comprising a visual representation of a heightened analysis element, according to an embodiment of a method of this invention;

FIG. 6 is a chart for use in identifying a prescription as a renewal according to an embodiment of a method of this invention;

FIG. 7 is a chart illustrating drugs identified as similar according to an embodiment of a method of this invention;

FIG. 9 illustrates an exemplary operating environment for implementation of various embodiments of the invention.

Figure 1:
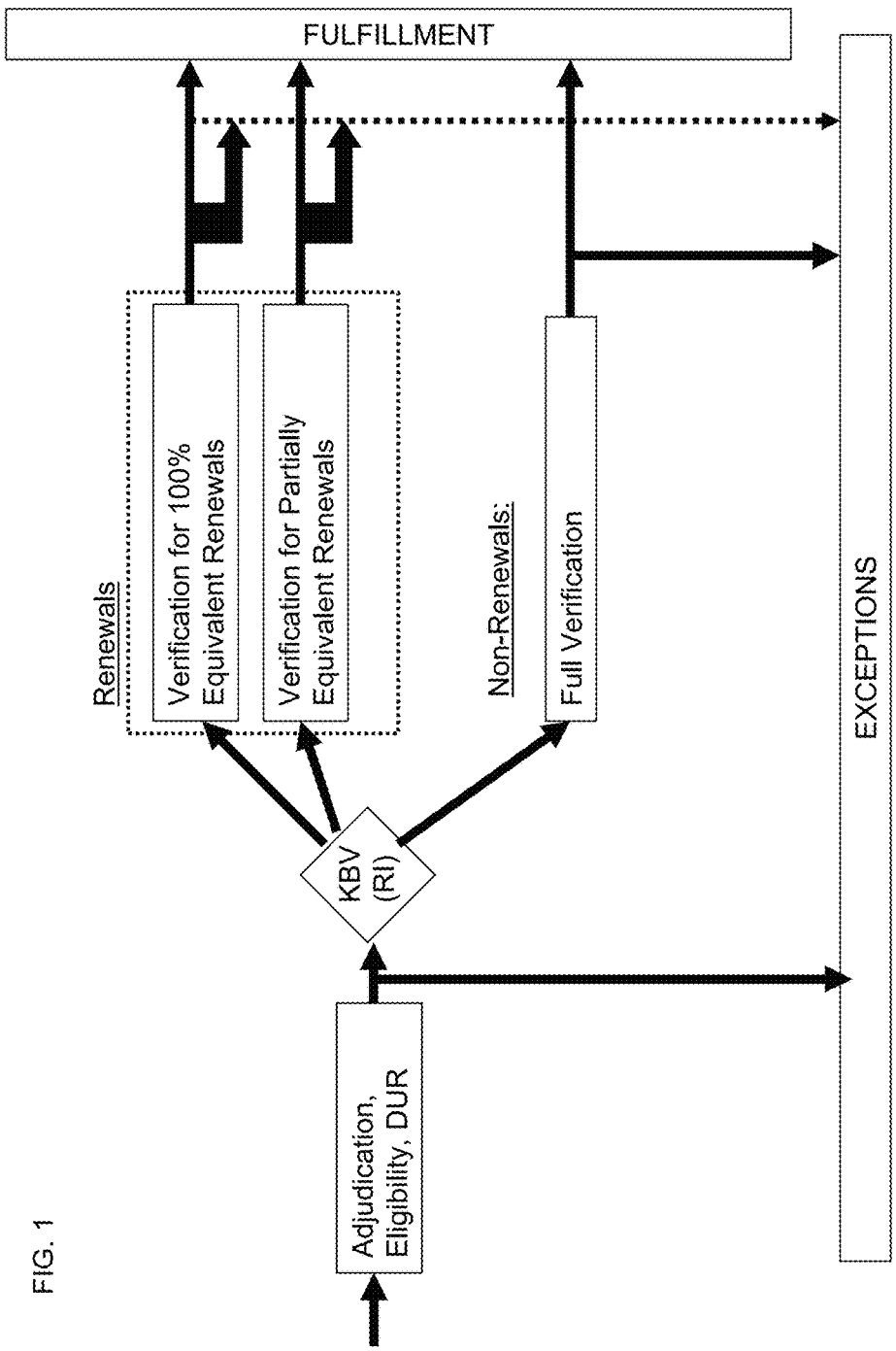
FIG. 1 is a flowchart of a method of processing prescriptions according to an embodiment of a method of this invention.
Figure 2:
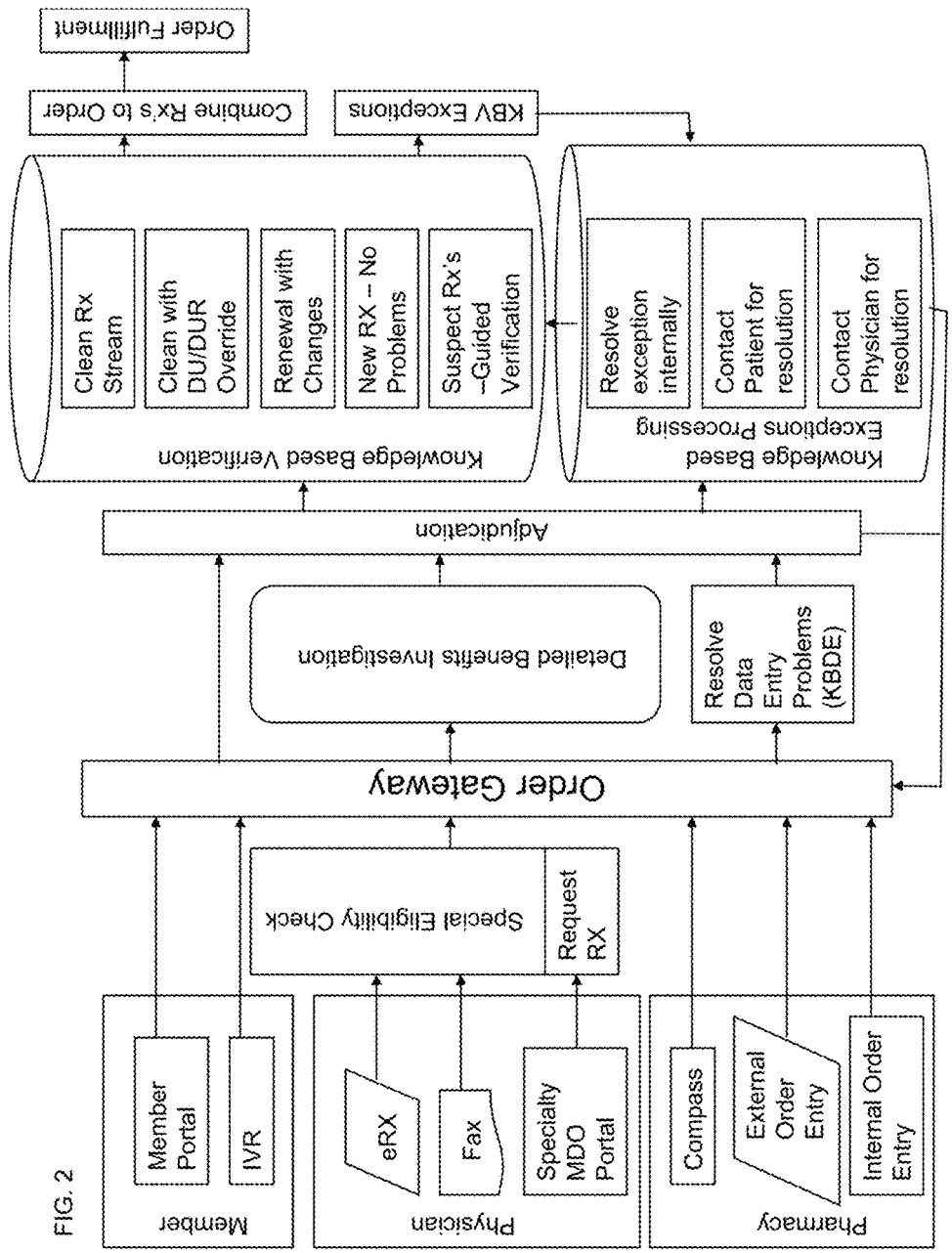
FIG. 2 is a flowchart of a method of processing prescriptions according to an embodiment of a method of this invention.

These drawings are provided for illustrative purposes and should not be used to unduly limit the scope of the claims.

DETAILED DESCRIPTION OF THE INVENTION

A party processing a prescription (referred to herein as a "processed prescription", the "current prescription" and the like) according to a method of this invention will be obtaining at least one heightened analysis element and/or an insignificant differences notice based on a comparison between the processed prescription and at least one similar historical prescription and/or will be obtaining at least one indicator representing a heightened analysis element or an insignificant differences notice.

A comparison between a processed prescription and one or more similar historical prescription, to establish at least one heightened analysis element and/or an insignificant differences notice, is typically based on a comparison of prescription element information of the processed prescription to prescription element information of the similar historical prescription (or set of similar historical prescriptions) for a set of prescription elements. Which prescription elements are selected for comparison may vary depending upon the purposes for which a method of this invention will be used, e.g., the specific error reduction and/or efficiencies a user may wish to achieve.

As discussed herein, the party processing a prescription will be a pharmaceutical professional; specifically, for purposes of this description, a person processing a prescription is a "pharmaceutical professional." When a pharmaceutical professional obtains an indicator of a heightened analysis element, that indicator serves to highlight a prescription element and its associated prescription element information for review and consideration by the pharmaceutical professional. Typically, and as illustrated by examples in the discussion that follows, a heightened analysis element is a prescription element in which the prescription element information of the processed prescription is different than the prescription element information of a similar historical prescription. An indicator of a heightened analysis element may comprise any appropriate means to identify the heightened analysis element to the pharmaceutical professional as such. For example, an indicator may comprise a visual representation of some or all of the prescription element information in which the prescription element information associated with the heightened analysis element is highlighted, provided in a distinctive color, font, and/or size of text, and/or accompanied by a notice (e.g., a notice that includes an explanation or link to an explanation for designation of the prescription element as a heightened analysis element) or other visual cue (e.g., a star or check mark). In another embodiment, an indicator may comprise an audio alert to the heightened analysis element. In a still further embodiment, an indicator may be found in the manner in which the prescription is routed for further processing, e.g., prescriptions in which a particular prescription element is identified as a heightened analysis element may be routed to a particular pharmaceutical professional for further processing and/or analysis; in such event, routing to that pharmaceutical professional may serve as an indicator of that heightened analysis element.

In the context of a comparison to a single similar historical prescription, "different" may mean, (1) not identical, (2) not substantially the same, (3) not similar, and/or any other appropriate determination of "different" under the circumstances. When a processed prescription is compared to a set of similar historical prescriptions then, in addition, "different" may refer to differences, distinctions, and the like between the prescription element information of the processed prescription and the set of prescription element information of the set of historical prescriptions that are statistically significant, as determined in accordance with known statistical analysis techniques.

In the event a comparison between a processed prescription and a similar historical prescription establishes that they are not different ("not different" meaning the same, substantially the same, similar, no statistically significant differences, or other appropriate meaning of "not different"), an insignificant differences notice (i.e., an indicator of an insignificant difference between the prescription element information of a prescription element of the processed prescription and the similar historical prescription or set of historical prescriptions) serves to convey this information to the pharmaceutical professional processing the prescription according to this invention. If the insignificant differences notice applies to enough of the prescription elements being compared, it may allow the pharmaceutical professional processing the prescription to review the processed prescription as a "renewal", a "partial renewal", or "a partially equivalent prescription" (depending upon the level of similarity between the prescription element information) even if not designated as such via prescription element information. As will be understood by those with skill in the art, a "renewal" prescription typically can be processed more efficiently than a "new" prescription. Thus, by identifying a prescription as the "same" as a historical prescription and thereby processing it as a renewal, significant efficiencies in the processing of that prescription can be realized.

Alternatively, an insignificant differences notice may apply to one or more prescription elements (but not the entire set of prescription elements), with the opposite effect of a heightened analysis element; in particular, informing the party processing a prescription that less attention and analysis may be devoted to these prescription elements than to others. Such a notice or indicator may take the form of one or more visual cues that de-emphasize a prescription element that is the subject of an insignificant differences notice, such as smaller or lighter text.

As noted above, a party processing a prescription according to the invention will obtain at least one heightened analysis element and/or an insignificant differences notice (and/or indicator thereof), that such party may use as a tool in processing such a prescription. A heightened analysis element or an insignificant differences notice is established based on a comparison between the processed prescription and one or more historical prescriptions that have been established as a similar historical prescription. Thus, a party processing a prescription according to the invention will be obtaining, directly and/or indirectly, a set of historical prescriptions and will be obtaining, directly and/or indirectly, at least one similar historical prescription from the set of historical prescriptions. Furthermore, a party processing a prescription according to the invention will be establishing, directly or indirectly, at least one historical prescription as a similar historical prescription and will be establishing at least an insignificant differences notice or a heightened analysis element based on a comparison between the processed prescription and the at least one historical prescription. As discussed below, in certain embodiments, an "insignificant differences notice" may take the form of designation (or further processing) of the current prescription as a renewal, partial renewal, or partially equivalent renewal. Similarly, a "heightened analysis element" may take the form of a designation (or further processing) of the current prescription as a new prescription.

A "historical prescription" is a prescription written (and, preferably, filled) before the processed prescription. The set of historical prescriptions obtained for use in a method of the invention may be any set of historical prescriptions reasonably likely to include at least one similar historical prescription. For example, the set of historical prescriptions may be some portion or all of the prescriptions previously filled and/or processed by the pharmacy at which the current prescription has been submitted. However, the set of historical prescriptions need not be directly available to the party processing the prescription. For example, in one embodiment a second party (e.g., a party with access to a substantial quantity of historical prescription data) receives a set of prescription data representing prescription element information from a first party (e.g., a retail pharmacy) and uses that data to establish an insignificant differences notice and/or a heightened analysis element and provides that insignificant differences notice and/or heightened analysis element to the first party for use in processing the prescription. Depending upon applicable rules, regulations, and or privacy concerns, the set of prescription data provided to the second party may exclude patient elements.

A subset of previously filled and/or processed prescriptions may be obtained as a "set of historical prescriptions." In some instances, the subset may be obtained based on one or more criteria that may be used to establish a historical prescription as a similar historical prescription. For example, a set of historical prescriptions may be historical prescriptions for the same patient for whom the current prescription was written. In such instance, whether the "set of historical prescriptions" is identified as the entire database used to locate prescriptions for that patient or as the set of historical prescriptions for that patient is largely irrelevant. If the former, then the step of creating a subset of historical prescriptions written for a particular patient may be described as part of "establishing one or more similar historical prescription."

Again, a party processing a prescription according to the invention will be "obtaining a set of historical prescriptions" regardless of whether the set of historical prescriptions has been directly identified or otherwise selected by such party, by one or more third parties, and/or by technological means. Note, however, that in an embodiment in which a first party (such as a retail pharmacy) obtains a heightened analysis element or an insignificant differences notice (and/or indicator thereof) from a second party, the first party likely will have indirectly obtained the set of historical prescriptions via the heightened analysis element or insignificant differences notice and may not have direct assess to the set of historical prescriptions.

Generally speaking, a "similar" historical prescription is one in which, for certain relevant prescription elements, the prescription element information of the historical prescription is the same or similar as the prescription element information for the prescription being processed according to a method of this invention. Thus, to establish a historical prescription as a similar historical prescription, prescription element information of the historical prescription is compared to prescription element information of the processed prescription.

As discussed in further detail the examples below, the criteria used to establish a historical prescription as similar and/or the selection of prescription element information to compare to identify similar historical prescriptions may vary depending upon the purposes for which a method of this invention will be used, e.g., the specific error reduction and/or efficiencies a user may wish to achieve. If a method of the invention will be used to determine whether a prescription can be processed as a "renewal", then, as a starting point, only those historical prescriptions that are for the same patient would be "similar" in that context. Furthermore, identifying a historical prescription as "similar" for this purpose preferably includes establishing similarity between drug element prescription information of the processed prescription and the historical prescription. If a method of this invention will be used to reduce errors, similarity between the patient element information of the processed prescription and a historical prescription may be less relevant.

There may not be (and need not be) a clearly defined endpoint to the step of, e.g., establishing one or more historical prescriptions as a similar historical prescription and, e.g., the step of establishing one or more of an insignificant differences notice and/or a heightened analysis notice. For example, having obtained a set of historical prescriptions, that set can be serially analyzed to further narrow the set of historical prescriptions (e.g., to one or more sets of similar historical prescriptions) to ultimately obtain the one or more similar historical prescriptions used to establish an insignificant differences notice and/or one or more heightened analysis element.

It should be noted that the prescription elements selected for comparison to determine whether a historical prescription is a similar historical prescription may be different than the prescription elements selected for comparison with the identified one or more similar historical prescriptions for purposes of establishing (and obtaining) at least one heightened analysis element and/or insignificant differences notice. For example, patient element information may be used to establish a historical prescription as a similar historical prescription and then drug element information may be used to establish an insignificant differences notice and/or heightened analysis element.

"Establishing" a historical prescription as a similar historical prescription and the like should be broadly understood to include use of procedures, criteria, and the like used in data analysis and reporting methods to establish, illustrate, and/or otherwise identify similarities between prescription element information of a prescription processed according to a method of this invention and a historical prescription. "Procedures" should be broadly understood to include methods, processes, techniques, schemes, formulas, algorithms, as well as the criteria embedded or used in or with any of the foregoing, to establish, determine, and/or otherwise identify similarities between one or more historical prescriptions and a processed prescription; "criteria" should be broadly understood to include standards, rules, measures, values, and the like. The process of "establishing" one or more historical prescriptions as a similar historical prescription may have been performed by the party processing the prescription, by a third party, and/or by technological means. In any event, a party processing a prescription according to the invention will be, directly or indirectly, "establishing a set of historical prescriptions" and "obtaining a set of historical prescriptions."

Similarly "establishing" an insignificant differences notice and/or a heightened analysis element and the like should be broadly understood to include use of procedures, criteria, and the like used in data analysis and reporting methods to establish, illustrate, and/or otherwise identify similarities and/or differences between particular prescription element information of a prescription processed according to a method of this invention and a historical prescription.

The comparison between the prescription being processed in accordance with a method of this invention and one or more similar historical prescriptions, based on which at least one heightened analysis element and/or an insignificant differences notice is established, may have been performed and the at least one heightened analysis element and/or an insignificant differences notice may have been established by the party processing the prescription, by a third party, and/or by technological means. Thus, the term "obtaining a heightened analysis element," "obtaining an insignificant differences notice," and the like should be broadly understood and include and/or refer to situations where the party processing the prescription is the party who has compared the prescriptions and established at least one heightened analysis element and/or an insignificant differences notice (with or without the use of technological means), as well as to situations where that party will be using comparisons performed and at least one heightened analysis element and/or an insignificant differences notice established by a third party and/or by technological means, and as well as to situations where the comparisons have been performed and at least one heightened analysis element and/or an insignificant differences notice have been established in part by the party processing a prescription and in part by a third party and/or by technological means.

As noted above, in one embodiment of the invention, a first party provides prescription element information to a second party, which the second party then uses to establish a heightened analysis element or insignificant differences notice based on a comparison of such prescription element information to a set of historical prescriptions, and which the first party then obtains from the second party for use as a tool in processing the prescriptions. This embodiment it allows the first party to receive the benefit of the second party's historical prescription information without directly accessing the information. For example, a first party, e.g., a pharmaceutical professional at a retail pharmacy, may receive prescription element information regarding a particular prescription to be filled and may transmit that data to a second party, e.g., a pharmacy benefit manager, which can then use that data (in a manner described above) to establish one or more similar historical prescriptions (the prescription information of which may or may not be otherwise available to the first party) and to establish a heightened analysis element and/or an insignificant differences notice, which can then be provided to the first party for the first party's use in filling the prescription. In this embodiment, the first party remains responsible for most or all of the steps involved in filling the prescription and uses the heightened analysis element and/or insignificant differences notice as a tool to assist the first party in safely and quickly filling the prescription.

Examples of particular procedures and criteria that may be used to establish an insignificant differences notice and/or a heightened analysis element are given below.

Computer-Implemented Methods

Although, in at least some embodiments, methods of this invention may be implemented without technological means, preferred embodiments are computer-implemented. In a particularly preferred embodiment, a database computer system comprises a memory storage device that stores (or is capable of storing) a database of historical prescriptions and an input system is capable of receiving as input prescription element information of a prescription to be processing in accordance with a method of this invention. A more detailed description of an exemplary operating environment follows and is illustrated on FIG. 9. FIG. 3 illustrates an input screen 30 a user may use to input prescription element information for a prescription to be processed in accordance with a method of this invention.

Furthermore, one or more computer programs (e.g., software, hardware, or firmware) or other technological means (e.g., a computer program that is a component of a distributed processing environment, discussed below) are generally preferred to perform the procedures to be used to establish a historical prescription as a similar historical prescription, compare a similar historical prescription to a processed prescription, and establish at least one heightened analysis element and/or insignificant differences notice. Particularly preferred are software programs provided by SAS Institute, Inc. Other commercially-available data analysis programs and/or mechanisms, programs, and the like may be used to perform the procedures of data analysis methods and thereby identify a historical prescription as a similar historical prescription, according to a method of this invention.

Preferably, a computer program transforms data generated from the comparison of the processed prescription and at least one historical prescription (or data generated from other steps in a method of this invention) that is used to establish a heightened analysis element and/or an insignificant differences notice to create one or more indicator (as describe above) of such heightened analysis element and/or insignificant differences notice, e.g., a visual indicator capable being displayed by one or more display devices (e.g., a display device composing a workstation system) and, thereby, presented to a user for analysis and/or use as a tool in processing a prescription. An example of a visual indicator 50 is provided on FIG. 5. As discussed above, such visual indicators preferably will comprise a visual representation of the at least one of a heightened analysis element 52 and/or an insignificant differences notice. An image of the processed prescription 54 and/or the one or more similar historical prescription compared to the processed prescription may also compose the visual representation. In other embodiments, a heightened analysis element, insignificant differences notice, and/or other information may be provided via audio representations capable of being transmitted by one or more output devices (such as a speaker). Unless the context requires otherwise, references to a heightened analysis element and/or an insignificant differences notice shall refer to visual, audio, and/or other representations (e.g., indicators) of such heightened analysis element and/or insignificant differences notice.

In one embodiment, a computing system (e.g., a personal computer or workstation) at a first location is adapted to receive prescription element information as input and is in communication with a second computing system (e.g., a distributed computing environment or one or more components thereof) at a second location, wherein the prescription element information is transmitted to the second computing system (e.g., via a wired or wireless communication network), the steps of establishing one or more similar historical prescriptions from a set of historical prescriptions (e.g., wherein data associated with the set of historical prescriptions is stored at a database system in communication with the second computing system) and of establishing at least one of a heightened analysis element or an insignificant differences notice is performed at the second computing system, and the second computing system transmits the heightened analysis element and/or insignificant differences notice to the first computing system to be presented to the user as output, e.g., to create a visual and/or audio indicator of the heightened analysis element and/or insignificant differences notice. In such an embodiment, transformation into an audio and/or visual indicator may take place at the first computing system, the second computing system, or both. It will be understood that the terms "first computing system" and/or "second computing system" may each to both hardware and software components of a single computer (e.g., a desktop, workstation, laptop, or handheld computing device) or to a network of computers and/or computing devices.

Data fields that correspond to various prescription elements may be provided and populated with data for prescription element information corresponding to a set of historical prescriptions in accordance with known data analysis methods. As will be understood, data fields preferably will be closely related to prescription elements. In one embodiment, data fields are identified as follows (descriptions follow the field identifiers), it being understood that the particular terms used to identify data fields are not critical.

Prescription Number: A number that uniquely identifies a prescription record.

Date Written: The date the prescription was written by the prescribing professional.

Patient Name: The first and last name of the patient.

Patient Date of Birth: The month, day, and year of the patient's birth.

Administrator: Used in uniquely identifying an individual patient.

Cardholder (Member) ID: The member ID number of the cardholder. Used in uniquely identifying an individual patient.

Person Number: Number assigned to a family member. Used in uniquely identifying a patient.

NDC/UPC: 11-digit National Drug Code number of the prescribed drug or the 11-digit Universal Product Code of the prescribed item.

Drug Name: Name of the dispensed drug.

Drug Strength: Strength of dispensed drug.

Drug Form: Form of dispensed drug.

Drug Manufacturer: Manufacturer of dispensed drug.

Substitution/DAW: Specifies if drug substitution is authorized or prevented due to preferences of the patient and/or prescribing professional.

Quantity Prescribed: Prescribed drug quantity.

Doctor Name: First and last name of the prescribing professional.

Doctor ZIP: ZIP code associated with the prescribing professional.

Doctor Fax: Facsimile number associated with the prescribing professional.

Doctor DEA Number: DEA number of the prescribing professional.

Sig: Sig instructions written on the prescription.

Date Filled: The date when the prescription was filled.

GCN: First Data Bank's Generic Code Number associated with the dispensed drug.

GPI: Medi-Span's GPI number associated with the dispensed drug.

Data for prescription element information for a prescription processed according to a method of this invention can similarly be used to populate data fields for such prescription. Referring to earlier classifications of prescription elements, using the above field identifiers, patient elements may include patient name, administrator, cardholder (member) ID, and/or person number. Drug elements may include NDC/UPC, GCN, GPI, drug name, drug strength, drug form, and/or drug manufacturers. Dispensing elements may include substitution/DAW, quantity prescribed, and/or Sig. Prescriber elements may include doctor name, doctor zip, and/or doctor DEA number.

As discussed in the examples below, the inventors have discovered unique methods of transforming prescription element information into data used to populate data fields that further enhances the increases in safety and efficiency achieved when processing a prescription according to a method of this invention.

Exemplary Operating Environment

Very generally, methods of the invention are preferably practiced, at least in part, in distributed computing environments, where tasks are performed by one or more processing devices that are linked through a communications network. In a distributed computing environment, program modules may be located in both local and remote memory storage devices. FIG. 9 is a diagram illustrating an exemplary operating environment for implementation of various embodiments of this invention. The exemplary operating environment 100 includes the following components: (a) a database computer system 120; (b) a distributed processing environment 122; and (c) one or more conventional personal computer or workstations 126, 128, 132 (a "workstation system" 124).

The database computer system 120 may be a computer system comprising hardware and software components that allow the system to serve as a database of data for historical prescription element information 130. The database computer system 120 will receive data for historical prescription element information, will be in communication with the distributed processing environment 122, and will allow retrieval of data for historical prescription element information for processing by the distributed processing environment 120 according to a method or system of the invention. Alternatively, a database computer system 120 may comprise a suite of distributed software services that provide access to the data for historical prescription element information through a computer network. More generally, the database computer system refers to those software and/or hardware components that facilitate storage of, receipt of, and access to data for historical prescription data.

The distributed computing environment 122 comprises hardware and/or software components that facilitate: (1) receipt of input (e.g., directly via human interface or indirectly from another computer device via a computer network), including input of prescription element information of a prescription to be processed according to a method or system of the invention; (2) access to the data representing historical prescription element information 130 stored at the database computer system 120; (3) performance of a method of the present invention (as described in detail herein) to establish at least one of an insignificant differences and/or a heightened analysis element; and (4) provision of the insignificant differences notice and/or heightened analysis element to the workstation system 124. The distributed computing environment 122 may also create an indicator of an insignificant differences notice and/or a heightened analysis element as discussed above, which indicator may be used as a tool in processing a prescription according to a method of this invention.

Optionally, a distributed processing environment 122 of the invention, having established an insignificant differences notice and/or heightened analysis element associated with a prescription being processed according to a method of this invention, may then output the prescription element information of such prescription to the database computer system 120 as data for historical prescription element information for use in a future iteration of a method of the invention. Additionally (or in the alternative), the distributed processing environment 120 may output generated heightened analysis elements and/or insignificant differences notices to an archival system 130 for later retrieval and review, data analysis and optimization, and/or tuning of the rules and criteria applied by a method of the invention to, e.g., result in establishing more effective or accurate heightened analysis indicators, insignificant differences notices, or other output.

In a system of the invention comprising multiple input facilities, e.g., a set of input devices configured to receive prescription element information and provide it to the distributed processing environment as input to that system, the distributed processing environment preferably will comprise multi-processing computing devices that are utilized to apply the specified method in parallel to the multiple input prescriptions.

In a preferred embodiment of the method of this invention, the distributed processing environment leverages a statistical computing software package or business-rules management and execution software package to apply the rules and criteria specified by the method to the data points for historical prescription element information and data points for prescription element information of the processed prescription to generate the desired output.

The workstation system 124 may comprise one or more a personal computers, computing workstations, and/or other set of hardware and software adapted to, optionally, receive prescription element information of a prescription to be processed according to this invention (e.g., by a user) and/or to receive as input the output produced by the distributed computing environment 122. The workstation system may also create an indicator of an insignificant differences notice and/or a heightened analysis element, as discussed above, which indicator may be used as a tool in processing a prescription according to a method of this invention; alternatively, if an indicator is created by the distributed computing environment 120, the workstation system 124 may display the indicator without further processing.

A workstation system can be used to receive input relating to a prescription to be processed according to a method of this invention. Alternatively, such information may be input by other means, such as an input system 134 (other than the workstation system) in communication with the distributed computing environment 122. An input system 134 is adapted to receive incoming prescription element information, optionally transform the prescription element information (e.g., by creating an electronic copy of the prescription element information and/or analyzing, interpreting, manipulating, and/or otherwise evaluating the prescription element information to produce data for the prescription element information, and output the prescription element information (as optionally transformed) to a distributed processing environment of the invention.

An embodiment comprising an input system that is separate from a workstation system may be particularly useful in an environment in which the pharmaceutical professional who uses an insignificant differences notice or heightened analysis element as a tool to process a prescription according to a method of the invention may not be directly involved in the process of receiving the prescription element information and/or providing it as input to the system.

In one embodiment the steps of: (1) receiving prescription information, (2) providing prescription element information as input, (3) receiving a heightened analysis element and/or insignificant differences notice (and/or indicator thereof), and (4) using the heightened analysis element and/or insignificant differences notice (and/or indicator thereof) as a tool in processing a prescription are performed at a first operating center (a "prescription fulfillment center", e.g., a retail pharmacy). In such an embodiment, the prescription fulfillment center (which may be physically located at one or more sites) will comprise a workstation system adapted to be in communication with one or more components of a prescription analysis center (discussed below). Such a workstation system may be adapted to receive prescription element information of the processed prescription; alternatively, the prescription fulfillment center may comprise a separate input system, wherein the input system is adapted to be in communication with one or more components of the prescription analysis center.

A prescription analysis center (which may be physically located at one or more sites) may comprise a distributed processing environment and/or such other components used to establish the heightened analysis element and/or insignificant differences notice based on a comparison between data for prescription element information of one or more historical prescriptions and of the processed prescription. The distributed processing environment and/or other component of the prescription analysis center will be adapted to be in communication with the prescription fulfillment center.

In any case, however, a pharmaceutical professional who processes a prescription using a heightened analysis element and/or an insignificant differences notices will have obtained that heightened analysis element and/or insignificant differences notice and will have, directly or indirectly, performed the steps to establish that heightened analysis element and/or insignificant differences notice.

In an embodiment, e.g., an embodiment comprising a preferred operating environment as described above, data for prescription element information of a historical prescription will be provided to the database system and used to populate data fields. Similarly, data for prescription element information of a processed prescription will be used by the distributed processing environment in performing the procedures and/or applying the criteria used to compare the prescription element information of the processed prescription to an established historical prescription or set of historical prescriptions and to establish a heightened analysis element and/or an insignificant differences notice. In some instances, a data point for prescription element information may be essentially the same as the prescription element information. In other instances, however, and as described in detail in the examples below, such information may benefit from further analysis, manipulation, interpretation, or other evaluation to become data and/or a data point for the prescription element information.

Examples

A renewal prescription typically can be processed more quickly than a new prescription. For example, some pharmacies will have a separated, expedited processing queue for renewal prescriptions. In this case, "renewal" refers to a prescription affirmatively designated as a renewal, e.g., by a prescribing professional.

Methods of the present invention may be used to identify prescriptions that may be appropriately processed as a "renewal" prescription, even though the prescription is received by the pharmacy as a new prescription. In this case, "renewal" refers to a prescription identified as "equivalent" to a similar historical prescription or, optionally, that is identified as "partially equivalent" to a similar historical prescription. In this preferred example, an embodiment of which is illustrated on FIG. 1, a "similar historical prescription", i.e., a historical prescription to be compared to the processed prescription to establish one or more heightened analysis elements and/or an insignificant differences notice, is one that is for the same patient and a similar drug.

In this context, "same patient" means the patient for whom the processed prescription was written and the person for whom the historical prescription was written are the same. "Same patient" can be established using any appropriate processes and/or criteria, e.g., comparisons of data for one or more patient identification elements information may be used to establish whether the patient is the same.

Preferably, in this embodiment, a drug is established as "similar" and, therefore, if for the same patient, a historical prescription may be established as a similar historical prescription, if the drugs of the historical prescription and the processed prescription are equivalent except for possible differences in: (a) brand/generic status; (b) form; and (c) strength. For example, using this definition of "similar" a 20 milligram ("mg") capsule of the drug sold under the brand name Prozac would be "similar" to a 40 mg tablet of fluoxetine.

As noted above, computer-implemented methods of the present invention are preferred and data analysis software is preferably used to compare data for prescription element information of a processed prescription to data for prescription element information for a set of historical prescriptions to identify similar historical prescriptions among the set. Accordingly, data for drug related prescription element information is preferably provided in a manner that will permit identification of drugs that are equivalent except for possible differences in: (a) brand/generic status; (b) form; and (c) strength (or that meet other definitions of "similar").

In one embodiment, a drug related prescription element is the novel "GCN-Group number" and information about the drug is used to establish data for that prescription element which is then used to populate that data field. GCN is a number assigned to each drug by First Data Bank in order to categorize drugs that are equivalent to each other. As a result, equivalent brand and generic drugs are assigned the same GCN value. However, GCN changes as either the strength or form of a drug changes. Thus, drugs identified as "similar" according to the standard set forth above would not have the same GCN.

The inventors have discovered an innovative method, outlined as follows, that may be used to map multiple related GCN values to a single GCN-Group number, which can then be used in comparing a processed prescription to a set of historical prescriptions to determine whether a historical prescription is for a "similar" drug, e.g., a drug that may differ in brand/generic status, form, and/or strength.

1. For any pair of drugs with the same drug name and different GCN (due to differences in strength, form etc.), establish and store a "link" between the two corresponding GCNs.
2. Assign a unique GCN-Group number to all GCNs that are connected to each other through a series of links.

Figure 8A:
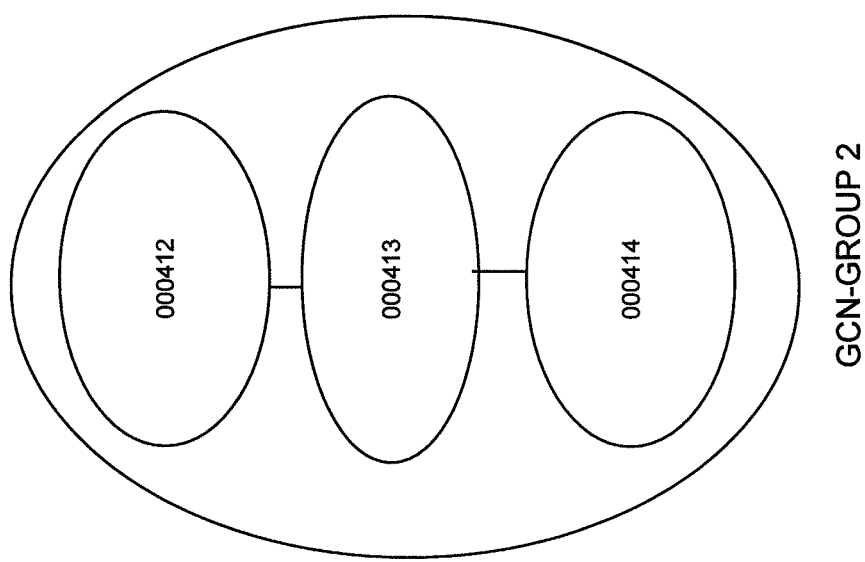
FIGS. 8a and 8b are illustrations of drugs identified as similar according to an embodiment of a method of this invention.
Figure 8B:
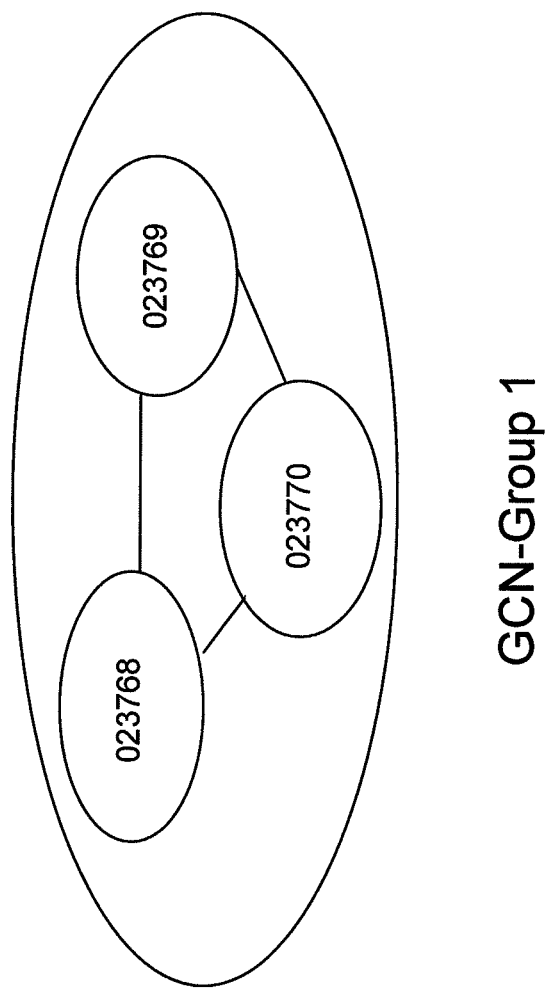

FIGS. 7, 8*a*, and 8*b* illustrate how the GCN-Group numbers can be generated for a set of drugs. FIG. 7 contains a list of drugs that can be partitioned into two subsets. The first subset (FIG. 8*b*) consists of different strengths of Lotrel (Amlodipine/Benazepril). The second subset (FIG. 8*a*) consists of different strengths of Lopressor (Metoprolol).

Note that the drugs in the first subset are associated with one of the three GCN values (23768, 23769, and 23770). Step 1 of the methodology links these GCN values to each other by identifying a common drug name (in this case Lotrel). Similarly, existence of common drug names indicates a link of GCN 412 to 413 and 413 to 414.

After Step 1 links related GCNs, Step 2 groups all GCN values that are connected to each other through a series of links. FIG. 7 illustrates the connected GCN values in a network structure and shows how connected GCNs can be assigned to a common GCN-Group number.

Alternatively, Medi-Span's Generic Product Identifier (GPI) may be used to identify similar drugs and, therefore, similar historical prescriptions. GPI number categorizes drug products by a hierarchical therapeutic classification scheme. It consists of 14 digits and contains 7 levels of drug information, each providing increasingly more specific information about the drug. The structure of GPI number is described below:

1. Drug Group: 12-xx-xx-xx-xx-xx-xx
2. Drug Class: 12-34-xx-xx-xx-xx-xx
3. Drug Subclass: 12-34-56-xx-xx-xx-xx
4. Drug Name: 12-34-56-78-xx-xx-xx
5. Drug Name Ext.: 12-34-56-78-90-xx-xx
6. Dosage Form: 12-34-56-78-90-12-xx
7. Strength: 12-34-56-78-90-12-34

The last 4 digit of GPI pertain to drug from and strength. If a "similar" drug is defined as one that is equivalent but for differences in brand/generic status, form, and/or strength, using just the first 10 digits of the GPI number may be used to identify a "similar" drug and, therefore, similar historical prescriptions. Thus, a drug related prescription element may be "truncated GPI" which, as a data field for a set of data for a particular historical prescription, may then be populated with the first ten digits of the GPI number. In addition, brand and generic versions of the same drug typically have the same first 10 digits of GPI.

In other embodiments, other definitions of "similar" may be appropriate and/or other methods may be used to promote software-implemented data analysis to determine whether a drug satisfies such a definition of "similar." For example, a drug may be identified as "similar" if it belongs to the same therapy class and/or class of drugs; e.g., setraline (another selective serotonin reuptake inhibitor) may be identified as "similar" to fluoxetine in some embodiments. In still other situations, a more restrictive definition may be preferred; for example, one drug may be similar to another only if the differences are limited to brand/generic status and form.

Having identified a similar historical prescription, a preferred next step in using a method of the invention to process a prescription as a "renewal" is to compare the processed prescription to the one or more identified similar historical prescriptions.

In a preferred embodiment, a data analysis algorithm, implemented in SAS for analysis purposes, is used for process this comparison and involves the following major steps:
 1. Group a set of historical prescriptions for each "same patient—similar drug" combination.
 2. For each group, sort all prescriptions with respect to the "date written" field.
 3. Process all records in each group sequentially. Specifically, for each prescription processed according to a method of this invention, search for a matching initial record within the same group, e.g., search for a historical prescription in which the prescription element information for patient identifying elements is the same and in which prescription element information for drug identifying elements is similar. If at least one similar historical prescription is found, then label the processed prescription as a renewal and label the most recent (according to date written field) similar historical prescription as the similar historical prior prescription.
 4. For each processed prescription labeled as a renewal, compare the data for its prescription element information to the data for the prescription element information of the obtained similar historical prescription. Store and maintain any such observed prescription element differences as "heightened analysis elements." If no differences are identified, store and maintain an "insignificant differences notice" for the processed prescription and the similar historical prescription.

Note that, in the method outlined above, the first three steps identify a similar historical prescription, i.e., identify the processed prescription as one to be processed as a "renewal." The last step identifies potential changes in the attributes of each renewal relative to its corresponding prior prescription, i.e., provides for establishing an insignificant differences notice and/or a heightened analysis notice.

If one or more heightened analysis elements are established when comparing a processed prescription to a similar historical prescription, then, in this example, such processed prescription can be identified as a partially equivalent renewal; in other words, it can be processed in a manner that is somewhat more expedited than a new prescription. A pharmaceutical professional can use indicators produced by the system (e.g., a distributed processing environment and/or workstation system), e.g., to view a visual depiction of any heightened analysis elements and, preferably, of the processed prescription and, optionally, the similar historical prescription.

If no differences are identified and an insignificant differences notice is produced, the processed prescription can be processed as an equivalent renewal. In certain embodiments, if a processed prescription and a similar historical prescription are established as not different, the processed prescription may be routed by the system (e.g., distribute processing environment) into the equivalent renewal queue; in that situation, placement into that queue may serve as an "insignificant differences notice" for purposes of the invention. FIG. 6 is a table that illustrates an example of circumstances in which a processes prescription and a similar historical prescription may be considered equivalent according to a method of this invention.

To the contrary, according to one embodiment of a method of this invention, if a prescription is not established as sufficiently similar to any historical prescription (or similar historical prescription) to warrant treatment as a renewal, the prescription may be processed as new prescription. In this exemplary embodiment, information generated during the comparison may not be provided to the pharmaceutical professional who completes processing the current prescription. Instead, the fact that the current prescription is being processed as a new prescription may function as an indicator of a heightened analysis element.

Other methods of identifying similar historical prescriptions and/or comparing a processed prescription to one or more identified similar historical prescriptions may be used. For example, in some embodiments, it may be preferable to index a set of historical prescriptions so that obtaining a similar historical prescription and comparing it to the processed prescription will be more efficient.

Other methods of manipulating information to create data used to populate prescription elements may further enhance efficiencies of methods of this invention. For example, acting on information provided in the prescription in the form provided by the prescribing professional, differences in SIG may be identified as "heightened analysis elements" (or may prevent a prescription from being processed as an equivalent renewal) when, in fact, there are no substantive differences between the Sigs. For example, the codes MD (for take 1 tablet daily), 1T/PO/QD (for take 1 tablet by mouth every day), 1T/QD (for take 1 tablet every day), 1T/PO/D (for take 1 tablet by mouth daily), and 1T/D (for take 1 tablet daily) might all be viewed as equivalent; however, a data analysis program in which the information in that form was used to populate data fields would not identify them as such. However, according to an embodiment of the invention, equivalent Sigs are transformed into an identical "transformed SIG code" that is used as the data point for the Sig data field, and, therefore, equivalent Sigs can be recognized as such. This may further improve the efficiencies offered by methods of this invention by generating more "insignificant differences notices", thereby reducing processing time.

Figure 4:
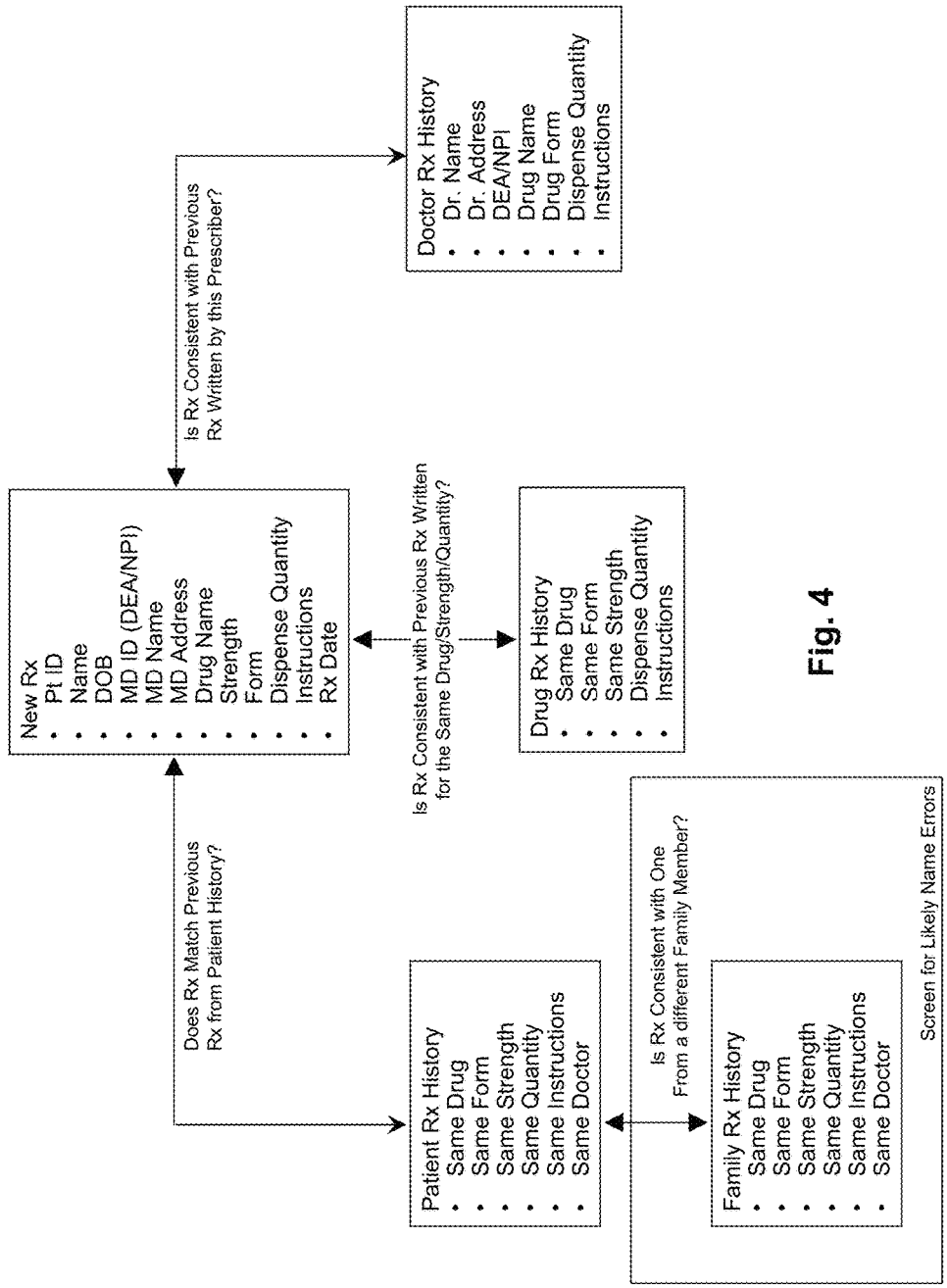
FIG. 4 is a flow chart illustrating alternate embodiments of methods of processing prescriptions according to this invention.

Other examples of uses of methods of this invention to reduce errors and improve efficiencies in processing prescriptions are illustrated on FIG. 4 and include the following:

A historical prescription may be identified as "similar" if it is for a family member of the patient and for the same or similar drug. A comparison of the processed prescription to such a similar historical prescription may generate, e.g., a heightened analysis element that, when analyzed by a pharmaceutical professional processing the prescription according to the invention, will aid the pharmaceutical professional in identifying errors in patient related elements; for example, it may reveal errors in the name of the patient.

A historical prescription may be identified as similar if the information for one or more of the drug elements is similar. In this example, prescription elements used in identifying similar drugs would be limited to a comparison of prescription element information of drug elements. Furthermore, in this example a method of the present invention is preferably used to identify a set of similar historical prescriptions; particularly preferred is a set of similar historical prescriptions large enough to provide statistically significant results when analyzed. Having identified such a set of similar historical prescriptions, prescription element information of that set can be compared to the prescription element information of the processed prescription to identify potentially significant differences (e.g., to establish one or more heightened analysis element). This comparison may include not only information for the drug elements selected to identify similar historical prescriptions, but information for other elements as well, such as patient elements relating to gender, age, and/or patient health elements. In this example, a heightened analysis element may inform a user of inconsistencies between the processed prescription and similar historical prescriptions for the same drug at the same strength. A heightened analysis element might be established if, for example, a comparison between the data for prescription element information of the processed prescription and data for prescription element information for the set of historical prescriptions reveals that the prescribed drug is rarely prescribed for a patient with the gender and/or age range of the patent for whom the processed prescription was written. Such a heightened analysis element (or its indicator) may be referred to as a "prescription error indicator".

Methods of the present invention may be used to establish heightened analysis elements that would aid in determining whether a processed prescription is consistent with historical prescriptions written by the same physician. Thus, in such an embodiment, a prescription might be "similar" if it is for the same doctor and same or similar drug. A heightened analysis element (e.g., a "prescription error indicator") might reveal, for example, differences in information for dispensing elements that might indicate an error has occurred at some point in the prescription processing (including an error upon creation of the prescription).

Heightened analysis elements and/or insignificant differences notices generated in accordance with either of the two foregoing examples might be particularly useful in an embodiment in which a first party (e.g., a retail pharmacy) obtains an insignificant differences notice or heightened analysis element from a second party based on a comparison of prescription element information of the processed prescription to historical prescription element information maintained by the second party, since a larger set of data for historical prescription element information would be more likely to produce a statistically significant result upon analysis. Furthermore, such types of insignificant differences notices or heightened analysis elements are not dependent upon having available prescriptions for the same patient (or, at least, those that include prescription element information that identifies the patient by name or other unique identifier).

The terms "first," "second," "third," "fourth," and the like in the description and in the claims, if any, are used for distinguishing between similar elements and not necessarily for describing a particular sequential or chronological order. It is to be understood that under appropriate circumstances the embodiments of the invention described herein are capable of operation in sequences other than those illustrated or otherwise described herein. Furthermore, the terms "include," "have," variations of them, and other similar terms are intended to cover a non-exclusive inclusion, such that a process, article, or apparatus that comprises a list of elements is not necessarily limited to those elements but may include other elements not expressly listed or inherent to such process, article, or apparatus.

Although certain illustrative embodiments and examples have been disclosed, it will be apparent from the foregoing disclosure to those skilled in the art that variations and modifications of such embodiments may be made without departing from the spirit and scope of the invention. Accordingly, it is intended that the invention should be limited only to extent required by the appended claims and the rules and principals of applicable law.

We claim:

1. A method for visually indicating distinct levels of possible errors in electronic prescriptions comprising:

accessing, on a processor of a first party computer, a current prescription for a drug, the current prescription associated with an individual;

transmitting the current prescription from the first party computer to a second party computer separate from the first party computer;

searching, on the second party computer, a plurality of historic prescriptions stored in a database to identify a similar historic prescription that is similar to the current prescription;

comparing, on the second party computer, a plurality of prescription fields of the current prescription with the plurality of prescription fields of the similar historic prescription to identify any field data differences, including insignificant differences and heightened differences, among the plurality of prescription fields;

recording, on the second party computer, a field comparison identifier based on a comparison of the plurality of prescription fields, the field comparison identifier identifying field data similarity or field data difference;

routing the current prescription using recordation of the field comparison identifier to a prescription fulfillment center with the field comparison identifier containing either an insignificant difference or a heightened difference with the current prescription being filled using a first process with the field comparison identifier containing the insignificant difference and a second process with the field comparison identifier containing the heightened difference; and filling the current prescription at the prescription fulfillment center using either the first process or the second process, wherein the field comparison identifier includes a visual field difference indicator that identifies a field of the plurality of prescription fields of the current prescription as including different field data than the field of the similar historic prescription; and the method further comprising generating a display including:
  a first sub-display with at least a portion of the plurality of prescription fields of the current prescription and the visual field difference indicator, and (i) the different field data, or (ii) both the field associated with the different field data and the different field data; and
  a second sub-display simultaneously displayed with the first sub-display and including an image of a reference document for the current prescription,
wherein routing includes routing after generating the display and addressing at least one possible error indicated in the first sub-display.

2. The method of claim 1, wherein searching the plurality of historic prescriptions comprises:
  utilizing field data contained in the plurality of prescription fields of the current prescription to search the plurality of historic prescriptions, the plurality of prescription fields including a prescription number field, a date written field, a patient name field, a patient date of birth field, an administrator field, a cardholder identifier field, a person number field, a prescribed item number field, a drug name field, a drug strength field, a drug form field, a drug manufacturer field, a substitution field, a quantity prescribed field, a doctor name field, a doctor zip code field, a doctor fax field, a doctor enforcement agency number, a SIG field, a date filled field, a generic code number field, a generic product identifier field, or combinations thereof; and
  identifying the similar historic prescription among the plurality of historic prescription based on utilization of the field data to search the plurality of historic prescriptions.

3. The method of claim 1, wherein searching the plurality of historic prescriptions comprises:
  utilizing field data contained in a plurality of individual fields of the current prescription to search the plurality of historic prescriptions, the plurality of individual fields including data regarding the individual; and
  identifying the similar historic prescription among the plurality of historic prescription based on utilization of the field data to search the plurality of historic prescriptions.

4. The method of claim 1, wherein searching the plurality of historic prescriptions comprises:
  utilizing field data contained in a plurality of drug fields of the current prescription to search the plurality of historic prescriptions, the plurality of drug fields including data regarding the drug; and
  identifying the similar historic prescription among the plurality of historic prescription based on utilization of the field data to search the plurality of historic prescriptions.

5. The method of claim 1, wherein searching the plurality of historic prescriptions comprises:
  utilizing field data contained in a plurality of individual fields, a plurality of drug fields, a plurality of dispensing fields, a plurality of prescriber fields, or combinations thereof of the current prescription to search the plurality of historic prescriptions, the plurality of individual fields including data regarding the individual, the plurality of drug fields including data regarding the drug, the plurality of dispensing fields including data regarding dispensing of the drug, the plurality of prescriber fields including data regarding a prescriber of the drug; and
  identifying the similar historic prescription among the plurality of historic prescription based on utilization of the field data to search the plurality of historic prescriptions.

6. The method of claim 5, wherein the plurality of individual fields includes a name field, an address field, an age field, a data of birth field, a gender field, a unique identifier field, an insurer field, a policy number field, a group insurance number field, a member number field, an employer field, a health plan administrator field, or combinations thereof,
  wherein the plurality of drug fields includes a drug name field, a drug strength field, a drug form field, a drug instructions field, or combinations thereof,
  wherein the plurality of dispensing fields includes a quantity prescribed field, a quantity dispensed field, a number of days supply field, a number of refills field, a generic substitutions allowed field, or combinations thereof, and
  wherein the plurality of prescriber fields includes a prescriber name, a prescriber address, a drug enforcement agency (DEA) number, a prescriber fax number, a professional association number, or combinations thereof.

7. The method of claim 1, wherein the field comparison identifier includes an insignificant differences identifier that identifies a field of the plurality of prescription fields of the current prescription as including similar field data relative to the field of the similar historic prescription.

8. The method of claim 7, wherein the similar field data of the field of the current prescription has no more than insignificant differences relative to field data of the similar historic prescription.

9. The method of claim 1, wherein the field is a SIG field, the SIG field including a SIG code associated with directions for preparation of the drug, use of the drug, or preparation and use of the drug, and
  wherein comparing the plurality of prescription fields comprises:
    translating the SIG code associated with the SIG field of the plurality of prescription fields of the current prescription, the similar historic prescription, or both the current prescription and the similar historic prescription to a same drug usage basis; and
    comparing the SIG field of the current prescription and the similar historic prescription based on translation of the SIG code.

10. The method of claim 1, wherein the field comparison identifier includes an insignificant differences identifier that identifies a first field of the plurality of prescription fields of the current prescription as including similar field data relative to the first field of the similar historic prescription and a field difference identifier that identifies a second field of the plurality of prescription fields of the current prescription as including different field data than the second field of the similar historic prescription, the method further comprising:
  generating a display including at least a portion of the plurality of prescription fields of the current prescription, a first visual indicator that identifies the first field associated with the similar field data, the similar field data or both the first field associated with the similar field data and the similar field data, and a second visual indicator that identifies the second field associated with the different field data, the different field data or both the second field associated with the different field data and the different field data.

11. The method of claim 1, wherein searching the plurality of historic prescription comprises:
   searching the plurality of historic prescriptions to identify a plurality of similar historic prescriptions, the plurality of similar historic prescriptions including the similar historic prescription and an additional historic prescription.

12. The method of claim 11, further comprising:
   identifying a most recent similar historic prescription among the plurality of similar historic prescriptions as the similar historic prescription.

13. The method of claim 12, wherein identification of the most recent similar historic prescription comprises:
   sorting the plurality of similar historic prescriptions based on a date written field of the plurality of similar historic prescriptions; and
   identifying the most recent similar historic prescription among the plurality of similar historic prescriptions as the similar historic prior prescription based on sorting of the plurality of similar historic prescriptions.

14. The method of claim 1, wherein accessing the current prescription comprises:
   receiving the current prescription for the drug via facsimile.

15. The method of claim 1, wherein accessing the current prescription comprises:
   receiving the current prescription for the drug electronically through a network.

16. The method of claim 1, wherein the similar historic prescription includes same field data, similar field data, or both same and similar field data in the plurality of prescription fields as at least some of the plurality of prescription fields of the current prescription.

17. The method of claim 1, wherein the similar historic prescription is associated with a different individual than the individual.

18. The method of claim 1, wherein the similar historic prescription and the current prescription are at least similar except for differences in brand/generic status, drug form, drug strength, or combinations thereof.

19. The method of claim 1, wherein the plurality of prescription fields includes a Generic Code Number (GCN) associated with the current prescription is different than the GCN associated with the similar historic prescription.

20. The method of claim 1, wherein the plurality of prescription fields includes a Generic Product Identifier (GPI) number associated with the current prescription matches the GPI number associated with the similar historic prescription for drug group, drug class, drug subclass, drug name, and drug name extension and differs from the GPI number associated with the historic prescription for strength or dosage form and strength.

21. The method of claim 1, wherein the drug associated with the current prescription is different than the drug associated with the similar historic prescription, and the drug associated with the current prescription is for the same therapy class, same drug class, or both same therapy class and drug class as the drug associated with the similar historic prescription.

22. The method of claim 1, wherein the plurality of historic prescriptions is a plurality of prescriptions associated with a same pharmacy as the current prescription.

23. The method of claim 1, wherein the plurality of historic prescriptions has been prescribed prior to the current prescription.

24. The method of claim 1, wherein searching the plurality of historic prescriptions to identify a similar historic prescription that is similar to the current prescription includes searching to identify a statistically similar historic historical prescription and using the statistically similar historic historical prescription to generate the field comparison identifier.

25. The method of claim 24, wherein the identified statistically similar historic historical prescription is not an exact match and an insignificant differences notice is generated and comparing includes identifying potential prescription errors.

26. A method comprising:
   accessing, on a processor of a first party computer, a current prescription for a drug, the current prescription associated with an individual;
   receiving the current prescription from a second party computer at the first party computer;
   searching, on the processor, a plurality of historic prescriptions to identify based on statistical significance a plurality of similar historic prescriptions, the plurality of similar historic prescriptions including a similar historic prescription and an additional historic prescription, the similar historic prescription being associated with a different individual than the individual, the drug associated with the current prescription is different than the drug associated with the similar historic prescription, and the drug associated with the current prescription is for the same therapy class, same drug class, or both same therapy class and drug class as the drug associated with the similar historic prescription;
   sorting, on the processor, the plurality of similar historic prescriptions based on a date written field of the plurality of similar historic prescriptions;
   identifying, on the processor, the most recent similar historic prescription among the plurality of similar historic prescriptions as the similar historic prior prescription based on sorting of the plurality of similar historic prescriptions, the plurality of historic prescriptions being been prescribed prior to the current prescription;
   comparing, on the processor, a plurality of prescription fields of the current prescription with the plurality of prescription fields of the similar historic prescription to identify any field data differences, including an insignificant difference or a heightened difference, among the plurality of prescription fields, wherein the insignificant difference has a greater degree of similarity than the heightened difference;
   recording, by the processor, a field comparison identifier based on a comparison of the plurality of prescription fields, the field comparison identifier identifying field data similarity or field data difference, the field comparison identifier including a field difference identifier that identifies a field of the plurality of prescription fields of the current prescription as including different field data than the field of the similar historic prescription, the field comparison identifier including an insignificant differences identifier that identifies a first field of the plurality of prescription fields of the current prescription as including similar field data relative to the first field of the similar historic prescription and a field difference identifier that identifies a second field of the plurality of prescription fields of the current prescription as including different field data than the second field of the similar historic prescription;

generating a display, on the first party computer, the second party computer or both the first party computer and the second party computer, including a first display and a second display, wherein the first display includes at least a portion of the plurality of prescription fields of the current prescription, a first visual indicator that identifies the first field associated with the similar field data, and (i) the similar field data or (ii) both the first field associated with the similar field data and the similar field data, and a second visual indicator that identifies the second field associated with the different field data, the different field data or both the second field associated with the different field data and the different field data, and wherein the second display shows a reference document for the current prescription for a drug;

routing the current prescription to a prescription fulfillment center based on recordation of the field comparison identifier with the current prescription with the heightened difference being processed differently than the current prescription with the insignificant difference or no difference in the field comparison identifier; and filling the current prescription at the prescription fulfillment center based on routing of the current prescription.

* * * * *